(12) United States Patent
Greim

(10) Patent No.: US 7,876,097 B2
(45) Date of Patent: Jan. 25, 2011

(54) LOCAL COIL ARRANGEMENT WITH MAGNETIC FIELD SENSOR AND MAGNETIC RESONANCE SYSTEM WITH SUCH A LOCAL COIL ARRANGEMENT

(75) Inventor: Helmut Greim, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 270 days.

(21) Appl. No.: 12/266,714

(22) Filed: Nov. 7, 2008

(65) Prior Publication Data
US 2009/0128149 A1 May 21, 2009

(30) Foreign Application Priority Data
Nov. 9, 2007 (DE) .................. 10 2007 053 429

(51) Int. Cl.
*G01V 3/00* (2006.01)
(52) U.S. Cl. ..................... 324/318; 324/309
(58) Field of Classification Search ......... 324/300–322; 600/410–435
See application file for complete search history.

(56) References Cited

U.S. PATENT DOCUMENTS

| | | | | |
|---|---|---|---|---|
| 5,006,804 A | * | 4/1991 | Dorri et al. | 324/320 |
| 5,045,794 A | * | 9/1991 | Dorri et al. | 324/320 |
| 5,760,583 A | * | 6/1998 | Sato et al. | 324/318 |
| 6,037,850 A | * | 3/2000 | Honmei et al. | 335/216 |
| 6,129,668 A | * | 10/2000 | Haynor et al. | 600/424 |
| 6,169,963 B1 | * | 1/2001 | Markov | 702/57 |
| 6,448,772 B1 | * | 9/2002 | Aoki | 324/307 |
| 6,452,374 B1 | | 9/2002 | Kreischer | |
| 7,230,428 B1 | | 6/2007 | Ishii | |
| 7,541,811 B2 | * | 6/2009 | Usagawa | 324/319 |

* cited by examiner

*Primary Examiner*—Melissa J Koval
*Assistant Examiner*—Dixomara Vargas
(74) *Attorney, Agent, or Firm*—Schiff Hardin LLP

(57) ABSTRACT

A local coil arrangement for a magnetic resonance apparatus has a support structure with an antenna arrangement and a sensor arrangement embedded in the support structure. The antenna arrangement has a number of magnetic resonance antennas. A magnetic resonance excitation signal can respectively be emitted by means of each magnetic resonance antenna and/or a magnetic resonance signal can respectively be received by means of each magnetic resonance antenna. The sensor arrangement has a number of magnetic field sensors and an evaluation circuit. The magnetic field sensors detect how large a static magnetic field is to which the local coil arrangement is exposed and output a corresponding output signal and supply a corresponding output signal to the evaluation circuit. The evaluation circuit determines a logical presence signal and outputs it. The value of the logical presence signal depends on whether a field strength of the static magnetic field is greater than a minimum field strength.

15 Claims, 3 Drawing Sheets

LOCAL COIL ARRANGEMENT WITH MAGNETIC FIELD SENSOR AND MAGNETIC RESONANCE SYSTEM WITH SUCH A LOCAL COIL ARRANGEMENT

BACKGROUND OF THE INVENTION

1. Field of the Invention

The present invention concerns a local coil arrangement for magnetic resonance applications, of the type wherein the local coil arrangement has a support structure in which the antenna arrangement is embedded, and the antenna arrangement has a number of magnetic resonance antennas, wherein a magnetic resonance excitation signal can respectively be emitted by means of each magnetic resonance antenna and/or a magnetic resonance signal can respectively be received by means of each magnetic resonance antenna.

The present invention furthermore concerns a magnetic resonance system of the type having a basic that generates a static basic magnetic field with a field strength that is spatially homogeneous within an examination region of the magnetic resonance system and that is greater than a minimum field strength, at least one local coil arrangement of the type described above that can be introduced into and removed from the examination region, and a control and/or evaluation device that, in terms of signaling, can be connected at least temporarily with the antenna arrangement of the local coil arrangement to emit magnetic resonance excitation signals and/or to receive magnetic resonance signals.

2. Description of the Prior Art

Local coil arrangements are used in order to excite magnetic resonances only locally and/or in order to detect previously excited magnetic resonance signals only locally but with better signal-to-noise ratio.

For use, the local coil arrangement is applied on an examination subject (often a person). The examination subject is hereby normally located on a patient bed. The local coil arrangement can alternatively be attached directly to the patient bed or to the examination subject. After the application of the local coil arrangement, the patient bed (including the examination subject located thereon and including the local coil arrangement) is introduced into the examination region of the magnetic resonance system, the desired examination is conducted and then the patient bed is brought out of the examination region again.

When they should emit a magnetic resonance signal or should receive a magnetic resonance signal, the magnetic resonance antennas of the local coil arrangement must be resonant at the Larmor frequency of the magnetic resonance system. Due to the fact that the travel range of the patient bed is normally greater than the length of the examination region of the magnetic resonance system, however, the operation the local coil arrangement is only reasonable when the local coil arrangement is located in the examination region. When the local coil arrangement is located outside of the examination region, the magnetic resonance antennas of the local coil arrangement would even have a disruptive effect. For this reason, the magnetic resonance antennas of the local coil arrangement are only activated when the local coil arrangement is located in the examination region. Otherwise they are deactivated. The activation and deactivation hereby ensues via corresponding activation of detuning circuits that are associated with the magnetic resonance antennas.

An additional problem in local coil arrangements is the number of signal channels required. Often many local coil arrangements are present, wherein only a portion of the local coil arrangements are located in the examination region at any point in time, however. Via time-accurate connection of the respective magnetic resonance antennas with the control and/or evaluation device, the number of the required transmission channels can be distinctly reduced.

Various procedures are known in the prior art for time-accurate tuning/detuning and for time-accurate connection with the control and/or evaluation device. For example, it is known to determine the positions of the local coil arrangements with the aid of magnetic resonance imaging. In this case a separate adjustment step is necessary for the position detection. After the adjustment, the corresponding local coil arrangements are wired and selected in a complicated matrix.

SUMMARY OF THE INVENTION

An object of the present invention is to provide possibilities by means of which a correct activation of the antenna arrangement of the respective local coil arrangement is possible in a simple and reliable manner.

This object is achieved according to the invention by a local coil arrangement having a sensor arrangement is embedded into the support structure in addition to the antenna arrangement. The sensor arrangement has a number of magnetic field sensors and an evaluation circuit. The magnetic field sensors detect how large a static magnetic field is to which the local coil arrangement is exposed and output a corresponding output signal. The magnetic field sensors supply their output signals to the evaluation circuit. The evaluation circuit determines a logical presence signal and outputs it. The value of the logical presence signal hereby depends on whether a field strength of the static magnetic field is greater than a minimum field strength.

The local coil arrangement of the magnetic resonance system according to the invention is fashioned as described above. The antenna arrangement thereof is at least temporarily connectable in terms of signaling with the control and/or evaluation device of the magnetic resonance system. The minimum field strength upon the exceeding of which the evaluation circuit of the local coil circuit checks the static magnetic field is hereby naturally identical with the minimum field strength that is exceeded within the examination region of the magnetic resonance system.

The evaluation circuit respectively determines a logical intermediate signal using the output signal of each magnetic field sensor. In this case the evaluation circuit determines the value of the logical presence signal dependent on the logical intermediate signals. The intermediate signals exhibit hysteresis. A more stable operation of the local coil arrangement can be achieved by this procedure.

The minimum number of magnetic field sensors is one. However, the number of magnetic field sensors is advantageously at least two. In this case, the intermediate signals of the magnetic field sensors are advantageously logically AND-linked.

The presence of at least two magnetic field sensors is in particular reasonable when the magnetic resonance system possesses a motorized, movable transport device and the at least one local coil arrangement is directly or indirectly connected in a stationary manner with the transport device. The transport device is normally linearly mobile, such that the introduction of the local coil arrangement in the examination region and the removal of the local coil arrangement from the examination region can be produced via linear movement of the transport device. In the event of the presence of at least two magnetic field sensors whose intermediate signals are logically AND-linked, it is therefore possible to arrange the magnetic field sensors within the support structure such that, given linear movement of the transport device, the local coil arrangement is inserted into the examination region and removed from the examination region in chronological succession, in particular before and after the antenna arrangement. Due to the presence of at least two magnetic field sensors, it can thus be ensured in a simple manner that the evaluation circuit outputs the presence signal when and only when the respective antenna arrangement is located entirely in the examination region of the magnetic resonance system.

A detuning circuit by means of which the respective magnetic resonance antenna can be detuned is normally respectively associated with each magnetic resonance antenna. In a preferred embodiment of the present invention, the presence signal is supplied from the evaluation circuit within the support structure to the detuning circuits, such that the detuning circuits are automatically activated and deactivated depending on the presence signal. With this procedure, an automatic detuning and tuning of the magnetic resonance antennas is possible.

Alternatively or additionally, it is possible for the presence signal to be output outside of the local coil arrangement. For example, a switching matrix that is arranged between the local coil arrangement and the control and/or evaluation device can be activated depending on the presence signal. It is also possible for the presence signal to be received by the control and/or evaluation device. In this case, the activation of the switching matrix and/or the activation of the detuning circuits can be conducted by the control and/or evaluation device, for example.

In a further preferred embodiment of the present invention, the presence signal is independent of the polarity sign of the static magnetic field. Due to this fact, an apparently incorrect orientation of the local coil arrangement can be counteracted.

The magnetic field sensors can be fashioned as arbitrary magnetic field sensors. They are advantageously fashioned as Hall sensors.

DESCRIPTION OF THE PREFERRED EMBODIMENTS

Figure 1:
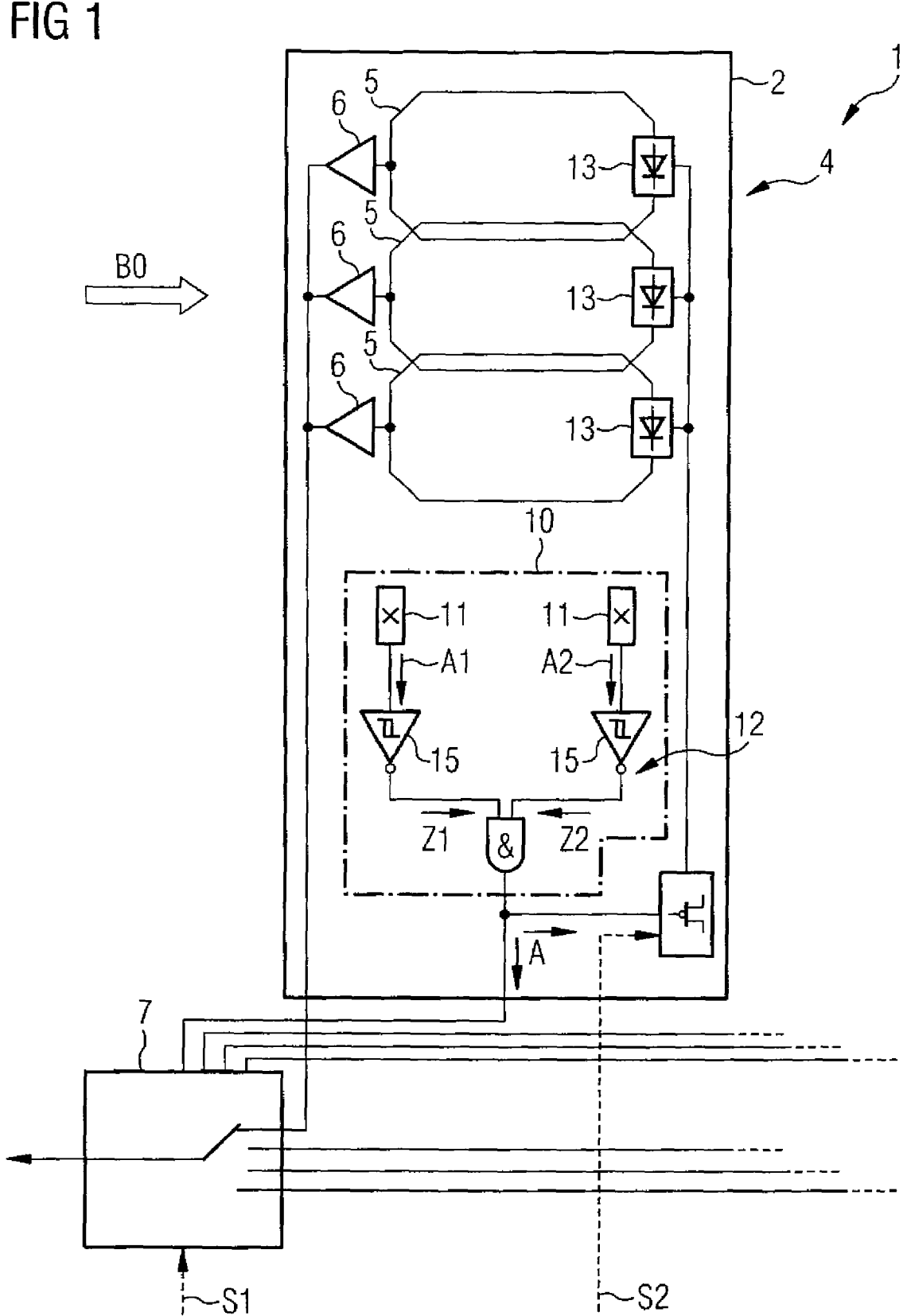
FIG. 1 schematically illustrates a local coil arrangement.

According to FIG. 1, a local coil arrangement 1 for magnetic resonance applications has a support structure 2. The support structure 2 can be rigidly fashioned. However, it is normally deformable so that it can be adapted to an examination subject 3 (see FIG. 4 and FIG. 5) in which it is used.

An antenna arrangement 4 is embedded in the support structure 2. The antenna arrangement 4 has a number of magnetic resonance antennas 5. A magnetic resonance excitation signal can respectively be emitted and/or a magnetic resonance signal can be respectively received by means of each magnetic resonance antenna 5. The magnetic resonance antennas 5 can be at least temporally connected (at least in terms of signaling) with a control and/or evaluation device 8 (see FIG. 4) of a magnetic resonance system 9 (see FIGS. 4 and 5), possibly via preamplifiers 6 and a switching matrix 7.

According to FIG. 1, the number of magnetic resonance antennas 5 is greater than one. The magnetic resonance antennas 5 are also coupled with one another. However, these two characteristics are not mandatory. The number of magnetic resonance antennas 5 could also be one. Furthermore, in the event of multiple magnetic resonance antennas 5, the magnetic resonance antennas 5 could also be capable of being operated independently of one another. The statement that a magnetic resonance excitation signal can respectively be emitted and/or a magnetic resonance signal can respectively be received by means of each magnetic resonance antenna 5 should also mean that, given (for example) four or eight magnetic resonance antennas 5, four or, respectively, eight magnetic resonance excitation signals can be emitted and/or four or, respectively, eight magnetic resonance signals can be received; in the case of only one magnetic resonance antenna 5, however, only a single magnetic resonance excitation signal can be emitted and/or a single magnetic resonance signal can be received.

According to FIG. 1, a sensor arrangement 10 is additionally embedded in the support structure 2. The sensor arrangement 10 possesses a number of magnetic field sensors 11 and an evaluation circuit 12. According to FIG. 1, at least two magnetic field sensors 11 are hereby present. However, this is not mandatory. Only a single magnetic field sensor 11 is required as a minimum. For example, the magnetic field sensors 11 can be fashioned as Hall sensors.

The magnetic field sensors 11 detect how large a static magnetic field B0 is to which the local coil arrangement 1 is exposed. They output a corresponding output signal A1, A2 that they supply to the evaluation circuit 12. Using the output signals A1, A2, the evaluation circuit 12 determines a logical presence signal A and outputs the logical presence signal A. The evaluation circuit 12 hereby determines the logical presence signal A depending on whether the field strength of the static magnetic field B0 is greater than a minimum field strength.

According to FIG. 1, a detuning circuit 13 is respectively associated with each magnetic resonance antenna 5. The respective magnetic resonance antenna 5 can be detuned by means of the respective detuning circuit 13. According to a preferred embodiment of the present invention, the presence signal A from the evaluation circuit 12 is supplied within the support structure 2 (thus without leaving the support structure 2) to the detuning circuits 12. In this case it is possible for the detuning circuits 13 to be activated and deactivated depending on the presence signal A. The magnetic resonance antennas 5 are thus tuned to the Larmor frequency of the magnetic resonance system 9 or not depending on the value of the logical presence signal A.

As an alternative or in addition to the activation of the detuning circuits 13, it is possible to output the presence signal A outside of the local coil arrangement 1. For example, the presence signal A can be supplied to the switching matrix 7 and be used there to activate the switching matrix 7. Alternatively, it is possible that the presence signal A is to be supplied to the control and/or evaluation device 8 which in this case receives the presence signal A. In this case, for example, the activation of the switching matrix 7 and/or of the detuning circuits 13 can ensue in that corresponding control signals S1, S2 are output by the control and/or evaluation device 8 to the switching matrix 7 and/or the detuning circuits 13, for example.

Figure 2:
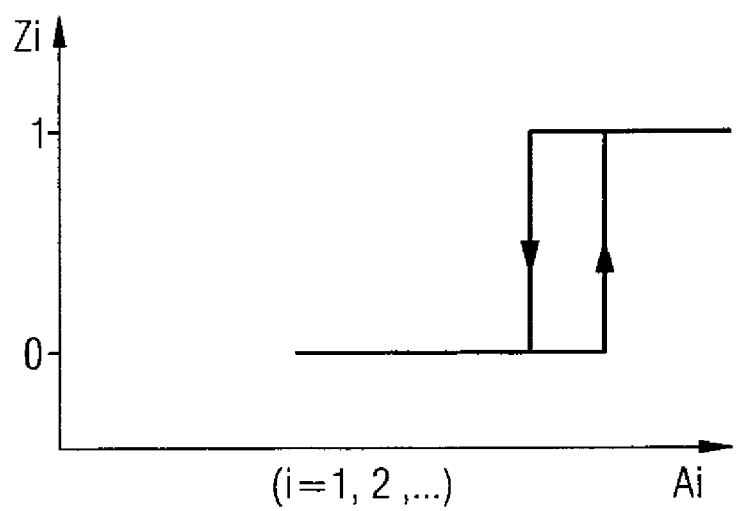
FIG. 2 is an intermediate signal magnetic field diagram.

According to FIGS. 1 and 2, using the output signals A1, A2 of the magnetic field sensors 11 the evaluation circuit 12 respectively determines a logical intermediate signal Z1, Z2. The evaluation circuit 12 then determines the value of the logical output signal A depending on the logical intermediate signals Z1, Z2. In particular, the evaluation circuit 12 can produce a logical AND-link of the intermediate signals Z1, Z2. The intermediate signals Z1, Z2 advantageously exhibit hysteresis according to FIG. 2.

Figure 3:
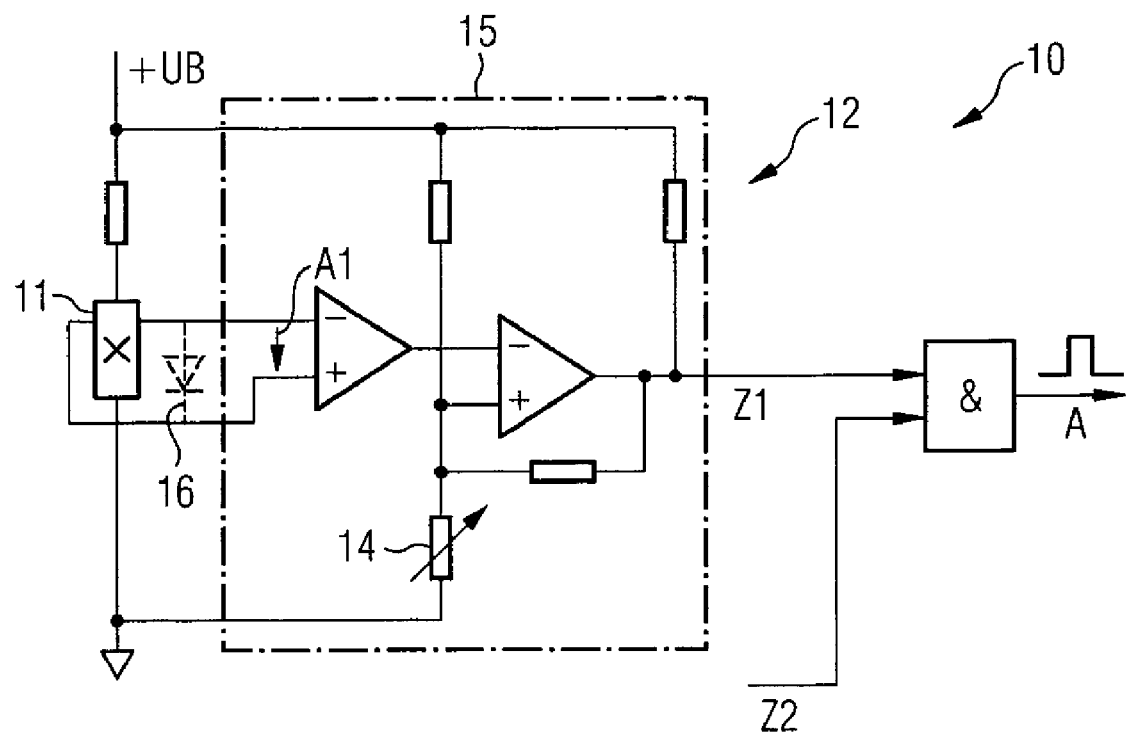
FIG. 3 schematically illustrates a sensor arrangement.

FIG. 3 shows a possible embodiment of the evaluation circuit 12 of the sensor arrangement 10. The representation from FIG. 3 generally uses typical circuit symbols, such that more detailed explanations with regard to FIG. 3 are not necessary. It is merely noted that the evaluation circuit 12 can in particular be an adjustment element 14 by means of which a threshold at which the intermediate signal Z1, Z2 of the respective magnetic field sensor 11 changes its logical value can be set. The minimum field strength can thus be set as a result of the value by means of the adjustment element 14. Insofar as multiple magnetic field sensors 11 are present (as shown in FIG. 1), the adjustment elements 14 are naturally set (by the individual pre-evaluation circuits 15 associated with the individual magnetic field sensors 11) such that all magnetic field sensors 11 act at the same minimum field strength.

The basic circuit shown in FIG. 3 detects the static magnetic field B0 afflicted [sic] with a polarity sign. Given a polarity reversal of the static magnetic field B0 (or a corresponding rotation of the local coil arrangement 1 by 180°), the magnetic field sensors 11 therefore do not act. However, without further measures it is known to experts in which manner the evaluation circuit 12 must be modified in order to be able to determine the presence signal A independent of the polarity sign of the static magnetic field B0. In the simplest case, for example, a rectifier circuit 16 can be arranged downstream of the magnetic field sensor 11 (as drawn with dashed lines in FIG. 3).

Figure 4:
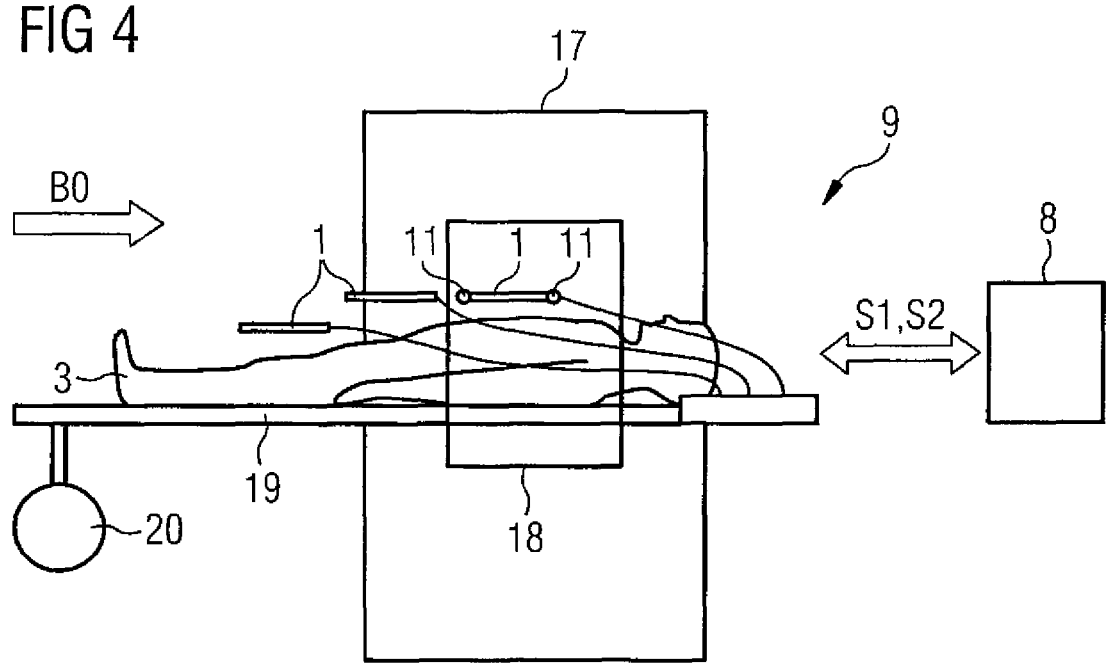
FIG. 4 schematically illustrates a magnetic resonance system.
Figure 5:
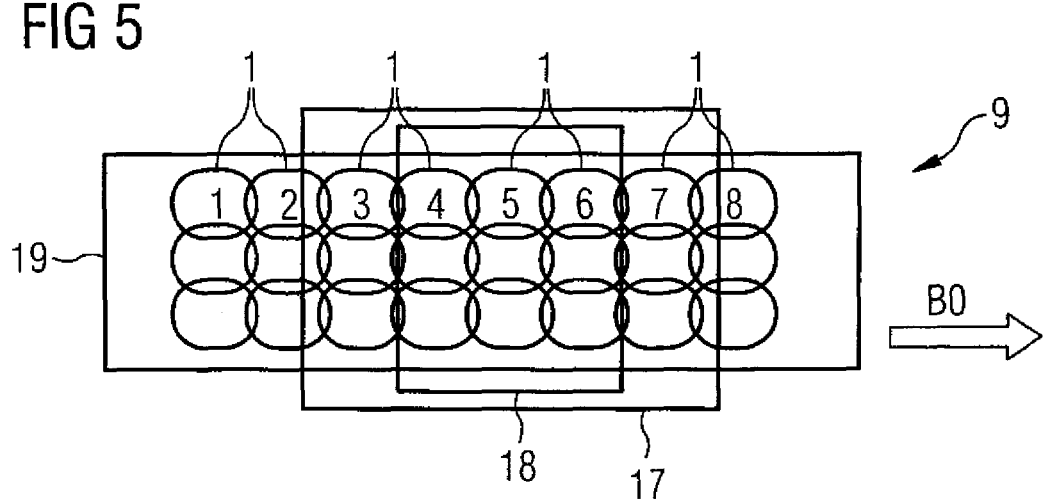
FIG. 5 schematically illustrates the magnetic resonance system of FIG. 4, from above.

The local coil arrangement 1 according to the invention can in particular be used in a magnetic resonance system 9 according to FIGS. 4 and 5. According to FIGS. 4 and 5, the magnetic resonance system 8 possesses a basic magnet 17. A static magnetic field (subsequently designated as a basic magnetic field) can be generated by means of the basic magnet 17. The basic magnetic field is the magnetic field that is detected by means of the magnetic field sensors 11. It is therefore likewise designated in the following with the reference character B0.

The field strength of the basic magnetic field B0 is dependent on the location. However, within an examination region 18 of the magnetic resonance system 9 the static basic magnetic field B0 is locally homogeneous and greater than the minimum field strength whose presence is detected by means of the sensor arrangement 10. As already mentioned, the magnetic resonance system 9 furthermore possesses at least one local coil arrangement 1 that is designed according to the invention and that can be introduced into and brought out of the examination region 18. For example, the magnetic resonance system 9 can possess a patient bed 19. The patient bed 19 corresponds to a transport device 19 in the sense of the present invention. The patient bed 19 is normally movable in a motorized fashion by means of a drive 20 (schematically shown in FIG. 4).

The local coil arrangement 1 is connected in a stationary manner with the patient bed 19, in some cases directly, in some cases indirectly via the examination subject 3. The patient bed 19 is normally linearly mobile by means of the drive 20. The introduction of the local coil arrangement into the examination region 18 and the removal of the local coil arrangement 1 from the examination region 18 can thus be produced via linear movement of the patient bed 19.

The magnetic resonance system 9 furthermore possesses the aforementioned control and/or evaluation device 8. The control and/or evaluation device 8 can be connected in terms of signaling with the antenna arrangement 4 of the local coil arrangement 1 to emit magnetic resonance excitation signals and/or to receive magnetic resonance signals (at least temporarily). The connection can hereby be static or dynamic (for example via the switching matrix 7).

As already mentioned, the sensor arrangement 10 advantageously possesses at least two magnetic field sensors 11 whose intermediate signals Z1, Z2 are AND-linked by the evaluation circuit 12 of the sensor arrangement 10. In particular in this case, the magnetic field sensors 11 are arranged in the support structure 2 so that they are offset from one another as viewed in the movement direction of the patient bed 19. It is thereby achieved that, given linear movement of the patient bed 19, the magnetic field sensors 11 are introduced into the examination region 18 and removed from the examination region 18 in temporal succession. In particular, the magnetic field sensors 11 can be arranged in the support structure 2 such that—as viewed in the movement direction of the patient bed 19—the antenna arrangement 4 is arranged between the magnetic field sensors 11. It is thereby achieved that the magnetic field sensors 11 are introduced into the examination region 18 or, respectively, removed from the examination region 18 before and after the antenna arrangement 4 upon linear movement of the patient bed 19. This procedure causes the presence signal A to be output only when the respective antenna arrangement 4 is located entirely in the examination region 18 of the magnetic resonance system 9.

The present invention exhibits many advantages. In particular, it is possible to select the respective local coil arrangements 1 located in the examination region 18 automatically and independently, i.e. to tune them to the Larmor frequency and to connect them with the control and/or evaluation device 8.

Although modifications and changes may be suggested by those skilled in the art, it is the intention of the inventor to embody within the patent warranted hereon all changes and modifications as reasonably and properly come within the scope of his contribution to the art.

I claim as my invention:

1. A local coil arrangement for magnetic resonance applications, comprising:
   a support structure;
   an antenna arrangement and a sensor arrangement embedded in said support structure;
   said antenna arrangement comprising a plurality of magnetic resonance antennas, each of said magnetic resonance antennas being configured to emit a magnetic resonance excitation signal and/or to receive a magnetic resonance signal;
   said sensor arrangement further comprising a plurality of magnetic field sensors and an evaluation circuit;
   said magnetic field sensors each detecting a magnitude of a static magnetic field in which said local coil arrangement is located and emitting a sensor output signal representing said magnitude; and
   said evaluation circuit receiving the respective output signals from the magnetic field sensors and determining a logic presence signal therefrom having a value dependent on whether a field strength of the static magnetic field is greater than a minimum field strength, and said evaluation circuit emitting said presence signal as an output.

2. A local coil arrangement as claimed in claim 1 wherein said evaluation circuit is configured to determine a logical intermediate signal from each output signal of each magnetic field sensor, and to determine the value of the logical presence signal from the logical intermediate signals.

3. A local coil arrangement as claimed in claim 2 wherein said intermediate signal exhibits hysteresis.

4. A local coil arrangement as claimed in claim 2 wherein said evaluation circuit is configured to logically AND-link intermediate signals for at least two of said magnetic field sensors.

5. A local coil arrangement as claimed in claim 1 comprising a detuning circuit connected to each magnetic resonance antenna that detunes the magnetic resonance antenna connected thereto, and wherein said presence signal is supplied to said detuning circuit from said evaluation circuit within said support structure to activate respective detuning circuits dependent on said presence signal.

6. A local coil arrangement as claimed in claim 1 wherein said presence signal is output by said evaluation circuit outside of said local coil arrangement.

7. A local coil arrangement as claimed in claim 1 wherein said evaluation signal generates said presence signal independently of a polarity of said static magnetic field.

8. A local coil arrangement as claimed in claim 1 wherein said magnetic field sensors are hall sensors.

9. A magnetic resonance system comprising:
   a basic magnet that generates a static basic magnetic field having a field strength that is spatially homogenous within an examination region, and that is greater than a minimum field strength; and
   a local coil arrangement comprising a support structure, an antenna arrangement and a sensor arrangement embedded in said support structure, said antenna arrangement comprising a plurality of magnetic resonance antennas, each of said magnetic resonance antennas being configured to emit a magnetic resonance excitation signal and/or to receive a magnetic resonance signal, said sensor arrangement further comprising a plurality of magnetic field sensors and an evaluation circuit, said magnetic field sensors each detecting a magnitude of a static magnetic field in which said local coil arrangement is located and emitting a sensor output signal representing said magnitude, and said evaluation circuit receiving the respective output signals from the magnetic field sensors and determining a logic presence signal therefrom having a value dependent on whether a field strength of the static magnetic field is greater than a minimum field strength, and said evaluation circuit emitting said presence signal as an output.

10. A magnetic resonance system as claimed in claim 9 comprising a motorized, movable transport device, and wherein said local coil arrangement is connected directly or indirectly with said transport device with a stationary connection.

11. A magnetic resonance system as claimed in claim 10 wherein said transport device is linearly movable, to introduce said local coil arrangement into said examination region and to remove said local coil arrangement from said examination region, and wherein said evaluation circuit is configured to logically AND-link intermediate signals from at least two of said magnetic field sensors to produce said presence signal.

12. A magnetic resonance as claimed in claim 11 wherein said presence signal is output by said evaluation circuit outside of said local coil arrangement.

13. A magnetic resonance system as claimed in claim 9 comprising, for each of said magnetic sensors, a detuning circuit connected thereto that is activatable to detune the magnetic resonance sensor, and wherein said control circuit is in communication with said detuning circuit and operates said detuning circuit dependent on said presence signal.

14. A magnetic resonance system as claimed in claim 13 comprising a switching matrix connected between said antenna arrangement and said evaluation circuit, said evaluation circuit emitting a control signal that controls switching of said switching matrix.

15. A magnetic resonance system as claimed in claim 9 comprising a switching arrangement connected between said antenna arrangement and said evaluation circuit, and wherein said presence signal is supplied to said switching matrix by said evaluation circuit to control switching of said switching matrix.

\* \* \* \* \*